United States Patent [19]
Yng-Wong

[11] Patent Number: 5,874,084
[45] Date of Patent: Feb. 23, 1999

[54] USING COMPLEX HERBAL FORMULATIONS TO TREAT HOT FLASHES

[76] Inventor: Quing Non Yng-Wong, 5524 MacArthur Blvd., Washington, D.C. 20016

[21] Appl. No.: 684,227

[22] Filed: Jul. 19, 1996

[51] Int. Cl.⁶ .................................................... A61K 35/78
[52] U.S. Cl. ........................................ 424/195.1; 514/899
[58] Field of Search ......................... 424/195.1; 514/899

[56] References Cited

U.S. PATENT DOCUMENTS

| | | | |
|---|---|---|---|
| 3,992,528 | 11/1976 | Graham | 514/5 |
| 4,096,254 | 6/1978 | Benson et al. | 514/177 |
| 4,613,591 | 9/1986 | Aburada et al. | 514/34 |
| 4,687,761 | 8/1987 | Liu | 514/26 |
| 4,738,956 | 4/1988 | Laurent et al. | 514/182 |
| 4,871,540 | 10/1989 | Kojima et al. | 424/195.1 |
| 5,055,297 | 10/1991 | Fujimaki et al. | 424/195.1 |
| 5,084,279 | 1/1992 | Kato et al. | 424/547 |
| 5,190,757 | 3/1993 | Kim | 424/195.1 |
| 5,225,203 | 7/1993 | Kim | 424/195.1 |
| 5,462,950 | 10/1995 | Fontana | 514/324 |
| 5,464,620 | 11/1995 | Zhao | 424/195.1 |
| 5,565,199 | 10/1996 | Page et al. | 424/195.1 |
| 5,569,459 | 10/1996 | Shlyanevich | 424/195.1 |

OTHER PUBLICATIONS

"Women's Diseases" by Fu ging–zhu, 1827, Quing Jing San formula.

Michael Murry, Information sheet for "Angelica Sinesis (Don Quai): An Herbal Formula of Symptoms of Menstrual Discomfort." Rosalba Belford/Courtney, Comparison of Chinese and Western Uses of Angelica Sinensis, Australian Journal of Med. Herbalism, vol., Dec. 1993.

*Primary Examiner*—Irene Marx
*Attorney, Agent, or Firm*—Nixon & Vanderhye P.C.

[57] ABSTRACT

Hot flashes (intense heat sensation, flushing, profuse sweating, palpitations, and/or sense of anxiety) in a menopausal woman may be substantially eliminated or ameliorated by administering to a woman in need of treatment an effective amount of ingestible material which has as substantially the only active ingredient a herbal complex. These exemplary herbal complex formula utilize a number of different species of herbs using the unique properties found in different parts of the plant, the root, the leaves, the aerial parts, the bark and the rhizomes.

2 Claims, No Drawings

USING COMPLEX HERBAL FORMULATIONS TO TREAT HOT FLASHES

BACKGROUND AND SUMMARY OF THE INVENTION

It is well recognized that women in many countries (the percentage often varying from country to country, however, due to dietary and lifestyle differences) experience what are commonly termed "hot flashes" at menopause. In fact more women seek medical treatment for hot flashes then for any other menopausal complaint. Hot flashes are defined in the literature as brief (often disabling) periods of intense heat sensation, flushing, profuse sweating, palpitations and/or sense of anxiety. Current therapy in the United States and some other countries for the treatment of hot flashes is estrogen replacement. However various estrogen treatment formulas have undesirable side effects (for example as described in U.S. Pat. No. 4,096,254), and usually estrogen replacement is not a practical or viable option for women who have had cancer or who are at high cancer risk levels for cancers that are affected by hormone levels. Also estrogen replacement is considered undesirable by some individuals, and a less extreme treatment medicine is desired by many.

According to the present invention, various herbal complexes are provided which can be administered to practice a method of substantially eliminating or ameliorating hot flashes. According to one aspect of the present invention this method comprises the step of administrating to a menopausal woman in need of treatment ingestible material that consists essentially of a complex herbal formulation in an amount effective to substantially eliminate or ameliorate brief periods of intense heat sensation, flushing, profuse sweating, palpitations, and for sense of anxiety (hot flashes). The complex herbal formulation is essentially free of human or animal origin estrogen or other female hormones. Substantially inert ingredients may also be added to the complexes to affect their taste, bulk, texture, or other attributes.

While a number of herbal complexes may achieve pharmacologically effective results according to the invention, three particular pharmacologically effective compositions have been identified. The first pharmacologically effective composition comprises a mixture of *Curculigo orchioides, Epimedium grandiflorum, Angelica sinensis, Morinda officinalis, Anemarrhena asphodeloides, Phellodendron amurense, Leonurus heterophyllus* and *Millettia dielsiana*, in a pharmacologically effective amount. The second formulation comprises a pharmacologically effective composition comprising a mixture of *Glycyrrhizae uralensis, Glycyrrhizae glabra, Astragalus membraneaceus, Poria cocos, Atractylodes lancea, Saussurea lappa, Polygala tenuifolia, Gardenia jasminoides, Cinnamomum cassia, Ziziphus jujuba, Panax ginseng,* and *Angelica sinensis,* in a pharmacologically effective amount. A third pharmacologically effective composition comprises a mixture of *Paeonia suffruticosa, Lycium chinense, Paeonia lactiflora, Paeonia lactiflora, Rehmannia glutinosa, Artemisia apiacea, Poria cocos, Phellodendron amurense, Bupleurum scorzoneraefolium, Coptis chinensis,* and *Cinnamomum cassia,* in a pharmacologically effective amount.

The formulations according to the invention may be administered in any conventional form including tablets, capsules, elixirs, as additives to food or beverages, or even can be made into a tea. The administered amount may vary widely depending upon the particular individual, but daily dosages of between 500–2000 mg are normally effective. Not all intensity, frequency, or both of most of the manifestations will be positively impacted.

DETAILED DESCRIPTION

Identification of specific herbal complexes that will perform effective pharmacologically without severe side effects is a painstaking and time consuming endeavor both in the initial development of the formulation and its subsequent testing. Three exemplary complex herbal formulations that have been identified and that may be utilized in the practice of the present invention have the following active compositions; in each case the active herbal components are expressed in weight percent, plus or minus 1% (for example "18%" means about "17–19 %"):

| FORMULA I | |
|---|---|
| *Curculigo orchioides* (curculigo) | 18% |
| *Epimedium grandiflorum* (epimedium) | 18% |
| *Angelica sinensis* (Dong quai) | 18% |
| *Morinda officinalis* (morinda root) | 11% |
| *Anemarrhena asphodeloides* (anemarrhena rhizome) | 11% |
| *Phellodendron amurense* (amur cork-tree bark) | 8% |
| *Leonurus heterophyllus* (Chinese motherwort) | 8% |
| *Millettia dielsiana* (miletta root and vine) | 8% |
| FORMULA II | |
| *Glycyrrhizae uralensis* (licorice root) | 2.7% |
| *Glycyrrhizae glabra* (licorice) | 2.7% |
| *Astragalus membraneaceus* (milk-vetch root) | 11.1% |
| *Poria cocos* (China root) | 11.1% |
| *Atractylodes lancea* (no English name) | 11.1% |
| *Saussurea lappa* (costus root) | 11.1% |
| *Polygala tenuifolia* (root of Chinese Senega) | 11.1% |
| *Gardenia jasminoides* (Cape Jasmine) | 5.6% |
| *Cinnamomum cassia* (Saigon cinnamon) | 5.6% |
| *Ziziphus jujuba* (seed of sour jujube) | 11.1% |
| *Panax ginseng* (ginseng root) | 5.6% |
| *Angelica sinensis* (Dong quai) | 11.1% |
| FORMULA III | |
| *Paeonia suffruticosa* (Cortex of Tree Peony Root) | 13.3% |
| *Lycium chinense* (Cortex of Wolfberry root) | 8.6% |
| *Paeonia lactiflora* (Peony root) | 13.3% |
| *Rehmannia glutinosa* (Root of Chinese foxglove) | 13.3% |
| *Artemisia apiacea* (Wormwood) | 8.6% |
| *Poria cocos* (China-root) | 13.3% |
| *Phellodendron amurense* (Amur cork-tree bark) | 8.6% |
| *Bupleurum scorzoneraefolium* (Hare's Ear root) | 8.6% |
| *Coptis chinensis* (Golden thread) | 8.6% |
| *Cinnamomum cassia* (Saigon cinnamon) | 4.2% |

Of course in addition to the active ingredients, the herbal complexes utilized according to the present invention may have any number of substantially inert ingredients which will vary depending upon the particular form by which the complex will be administered. Normally the complex is administered in the form of ingestible tablets or capsules which are swallowed with water, although the complex active ingredients may be mixed with food or beverage items and eaten or drunk, or in extreme cases may be introduced directly into the bloodstream using a hypodermic needle, I.V., or the like. The dose may vary depending upon the size, age, and condition of the woman being treated and the particular herbal complex utilized, but normally between about 500–2000 mg of active herbal complex is administered per day, with part of the total dose preferably taken at two or more different times during the day.

A typical manner of processing herbs to produce Formula I may be as follows, although a wide variety of different known processing techniques may be utilized depending upon the exact form of the material desired, and the availability of material or equipment:

The powder end product of Formula I is typically a 1:1 extract. Testing of raw materials used is conducted using standard organoleptic, High performance Liquid Chromatography, and microbiologic methods. The solvent mixture used for extractions for herbs used in Formula I is about 95% SDA 3C and about 5% potable water. SDA 3C is specifically denatured alcohol composed of 95% ethanol and 5% isopropyl. The extraction method is thermokinetic maceration, specifically about 180° F. for about three hours, plus warm up and cool down.

Following extraction, a sample is tested for the percentage of dissolved solids recovered. This is compared with the specified standards and, when necessary, the processing is continued until the standards are reached. The base material of the extract is marc; no rinse of the extracted powder is required. The miscella is distilled. The distilled total miscella is dehydrated onto the base material. This receives a final milling (1/32" screen) in a sanitary stainless mill, using a vacuum system to transport the product directly into the final containers. Samples are taken for quality control tests which are visual, taste, microbiologic and High Performance Liquid chromatography. Samples are also taken for permanent record. That material is readily made into tablets, or placed in ingestible capsules, e.g. about 300 mg per capsule.

When producing the herbal complex pursuant to exemplary Formula II, exemplary processing techniques that might be followed are:

The powder and end product of this formula is also typically a 1:1 extract. Testing of raw materials used is conducted using standard organoleptic, High Performance Liquid Chromatography and microbiologic methods. The solvent solution is preferably about 95% SDA 3C and 5% water.

The herb and the solvent are added together in the extract processor for processing. The supernatant liquid of solvent and solids is drained into the holding/settling tank where the volume is measured and the solids content is determined by analysis. Samples are drawn of both and liquid supernatant and sediment for microbiologic testing. The supernatant liquid is pumped through a 100 mesh liquid filter into the Sanitizing vessel. The liquid is processed for a minimum of four hours at the boiling temperature of about 178° F. The volume of the liquid is measured and a solids analysis is done. A sample is drawn for microbiologic testing. The liquid is pumped through a 100 mesh filter and sprayed into the vacuum dryer, using volume and solids data to adjust the product to the desired concentration for the finished product. The resulting material is dried. The processor is emptied into sanitary bulk bins or barrels and transported to milling. A pre-grind sample is drawn for biologic testing. The material is milled in a sanitary stainless steel milling system using a 1/16" screen. The material is unloaded from the mill system directly via Vac-u-Max collector into double lined 44gallon fiber drums. A sample is drawn from each container for biologic testing. Typical microbiologic requirements are:

|  | Limits |
| --- | --- |
| Aerobes | max. 10,000/g |
| Coliform | negative |
| Salmonella | negative |
| *E. Coli* | negative |
| Yeast | max. 100/g |
| Mold | max. 100/g |

The utilization of complex herbal formulations for the elimination or amelioration of hot flashes has been shown to be effective through testing, in some cases over a period of more than a year. Formula I was administered to a number of menopausal women in need of treatment. The following Table I represents an exemplary experience for three such menopausal women (i.e. who stated that hot flashes were a primary problem in menopause). As the Table reports, two of the three women experienced vast improvement. Neither reported any side effects, nor were any observed in clinical examinations. The third patient reported pain in her head during the month that she took the complex, and no significant relief, therefore treatment of her was discontinued after a month.

TABLE I

Experience with Formula I

| Patient Age | Dose | Duration | Why Taken | Effects | Side Effects |
| --- | --- | --- | --- | --- | --- |
| 63 | two 2×/day | 9 mos. | Hot flashes | Controlled (ameliorated) hot flashes | None |
| 43 | three 2×/day | 1 mo. | Irregular cycle Occasional hot flashes | None | Cycle became more irregular Shooting pains in head |
| 49 | three 2×/day | 16 mos. | Severe hot flashes - 6– 8×/night | Eliminated hot flashes More energy Less weepiness Short term memory improved | None |

The dose in Table I is expressed in the form of capsules, each containing approximately 300 mg of the active herbal complex. The duration is the approximate length of time over which the formulation was given.

Formula II as described above was also administered in tests. As reported in Table ll all four of the exemplary women treated found that their hot flashes were ameliorated. While some side effects were reported by two of the patients, there were no serious negative side effects, and the amelioration or elimination of the hot flashes was considered by the women with minor side effects as much more desirable than the negative aspects of the side effects.

TABLE II

The Experience with Formula II

| Patient Age | Dose | Duration | Why Taken | Effects | Side Effects |
| --- | --- | --- | --- | --- | --- |
| 55 | 2/day | 5 mos. | Hot flashes Insomnia head "flutters" - thought was going crazy | Decreased intensity & frequency of hot flashes | Increased premenstrual breast tenderness |
| 54 | 2–3/ day | 5 mos. | Hot flashes | Eliminated hot flashes for 3–4 mos. | Dry skin |
| 51 | one 2×/day | 4 mos. | Hot flashes | Decreased frequency & intensity of hot flashes | None |
| 49 |  |  | Hot flashes | Some diminishing of hot flashes | None |

The dose is expressed in the form of capsules, each containing approximately 300 mg of the herbal complex. The duration is the approximate length of time over which the formulation was tested.

While the herbal formulations according to the invention are effective when administered alone, for some patients they may be given or utilized in conjunction with human or animal estrogen, or other female hormone, containing chemicals, or other conventional therapies.

While the invention has been herein shown and described in what is presently considered to be the most practical and preferred embodiment thereof it will be apparent to those ordinary skill in the art that many modifications may be made thereof within the scope of the invention, which scope is to be accorded the broadest interpretation of the appended claims so as to encompass all equivalent methods and products.

What is claimed is:

1. A method of treating brief periods of at least one of intense heat sensation, flushing, profuse sweating, palpitations and sense of anxiety in a menopausal woman in need of treatment comprising administering to said menopausal woman an ingestible complex herbal formulation having active ingredients consisting essentially of a pharmacologically effective mixture expressed in weight percent as follows:

| | |
|---|---|
| Cortex of *Paeonia suffruticosa* | about 12.3–14.3% |
| Cortex of *Lycium chinense* | about 7.6%–9.6% |
| Root of *Paeonia lactiflora* | about 12.3–14.3% |
| Root of *Rehmania glutinosa* | about 12.3–14.3% |
| *Artemisia apiacea* | about 7.6%–9.6% |
| *Poria cocos* | about 12.3–14.3% |
| Bark of *Phellodendron amurense* | about 7.6%–9.6% |
| Root of *Blupleurum scorzoneraefolium* | about 7.6%–9.6% |
| *Coptis chinensis* | about 7.6%–9.6% |
| *Cinnamomum cassia* | about 3.2–5.2%. |

2. A complex herbal formulation for the treatment of brief periods of at least one of intense heat sensation, flushing, profuse sweating, palpitations and sense of anxiety in a menopausal woman in need of treatment consisting essentially of a pharmacologically effective mixture expressed in weight percent as follows:

| | |
|---|---|
| Cortex of *Paeonia suffruticosa* | about 12.3–14.3% |
| Cortex of *Lycium chinense* | about 7.6%–9.6% |
| Root of *Paeonia lactiflora* | about 12.3–14.3% |
| Root of *Rehmania glutinosa* | about 12.3–14.3% |
| *Artemisia apiacea* | about 7.6%–9.6% |
| *Poria cocos* | about 12.3–14.3% |
| Bark of *Phellodendron amurense* | about 7.6%–9.6% |
| Root of *Blupleurum scorzoneraefolium* | about 7.6%–9.6% |
| *Coptis chinensis* | about 7.6%–9.6% |
| *Cinnamomum cassia* | about 3.2–5.2%. |

* * * * *